United States Patent [19]

Chang et al.

[11] 4,373,036

[45] Feb. 8, 1983

[54] DENTURE FIXATIVE COMPOSITION

[75] Inventors: Tiang-Shing Chang, Westfield; Lucy J. Zientek, Bayonne; Arthur Viningauz, Irvington; Marcy L. Scheps, Perth Amboy, all of N.J.

[73] Assignee: Block Drug Company, Inc., Jersey City, N.J.

[21] Appl. No.: 332,890

[22] Filed: Dec. 21, 1981

[51] Int. Cl.$^3$ .............................................. C09J 3/04
[52] U.S. Cl. .................................... 523/120; 523/118; 524/42; 524/43; 525/328; 526/271; 433/168; 433/180; 260/998.11; 106/35
[58] Field of Search ................. 523/120, 118; 524/42, 524/43; 433/168, 180; 260/998.11; 525/328; 526/271; 106/35

[56] References Cited

U.S. PATENT DOCUMENTS

| | | | |
|---|---|---|---|
| 2,894,921 | 7/1959 | Jones | 525/328 |
| 2,978,812 | 4/1961 | Rosenthal | 523/120 |
| 2,985,625 | 5/1961 | Jones | 526/271 |
| 3,003,988 | 10/1961 | Germann et al. | 523/120 |
| 3,511,798 | 5/1970 | Isaacson et al. | 525/328 |
| 3,833,518 | 9/1974 | Rubin et al. | 523/118 |
| 3,868,432 | 2/1975 | Keegan et al. | 523/120 |
| 3,926,870 | 12/1975 | Keegan et al. | 523/120 |
| 3,936,402 | 2/1976 | Keegan et al. | 523/120 |

*Primary Examiner*—Lucille M. Phynes
*Attorney, Agent, or Firm*—Ostrolenk, Faber, Gerb & Soffen

[57] ABSTRACT

A denture fixative composition contains a dentally acceptable excipient and an effective fixative amount of a fixative mixture comprising hydroxypropyl cellulose and at least one partially neutralized alkyl vinyl ether-maleic acid or anhydride copolymer, optionally partly crosslinked, or a partially neutralized, optionally partly crosslinked polyacrylic acid or a precursor combination of the copolymer or polyacrylic acid, neutralizing agents, and optionally crosslinking agents, which is adapted to form the fixative *in situ*, or polyethylene oxide.

16 Claims, No Drawings

DENTURE FIXATIVE COMPOSITION

BACKGROUND OF THE INVENTION

There are a number of desirable characteristics of a denture fixative composition. One extremely desirable attribute is that it develops a high degree of tack upon contact with saliva in order that the dentures be held in place as soon as they are seated in the mouth. It is also highly desirable that the mucilage is spread over the denture-mucosa interface in order to effectively seal the denture in place and that the mucilages possess sufficient cohesive strength to withstand the stresses of mastication which act to rupture the seal and thus dislodge the denture. The denture fixative must also exhibit sufficient resistance to degradation under the extreme environmental temperature changes which occur in the oral cavity during such common actions as drinking coffee or other hot beverages.

Eberhard et al., in U.S. Pat. No. 2,997,399, teaches a dental fixative composition which is based on the use of hydroxyethyl cellulose and which also preferably contains methyl cellulose and polyacrylamide. The patent teaches that the hydroxyethyl cellulose should have an average degree of substitution of between 0.4 and 4.5 ethylene oxide groups per anhydroglucose unit. The patent further states that substantially equivalent results might be possible to obtain if only a minor proportion of the ethylene oxide groups are replaced with propylene oxide groups. However, the ethylene oxide cannot be replaced by propylene oxide at least as regards all or a substantial major portion of the ethylene oxide.

It has now been discovered that hydroxypropyl cellulose can be used in a denture fixative composition when combined with certain partially neutralized, optionally crosslinked polyacrylic acids or partially neutralized alkyl vinyl ether—maleic acid or anhydride copolymers, optionally crosslinked, or polyethylene oxide.

Numerous pharmaceutical formulations have employed polyacrylic acid and the use thereof has, in the past, been primarily directed to the exploitation of its thickening, suspending and emulsifying capabilities when the polymer is partially or wholly neutralized in amide or hydroxy solvents with an inorganic base, water soluble amine or some other combination thereof. In aqueous systems, the partially or wholly neutralized polyacrylic acid generates a gel which has low cohesive strength with a structure that may be easily ruptured when it is subjected to stresses such as those that occur during mastication.

U.S. Pat. No. 3,003,988 describes a dental fixative composition in which the dental fixative is a mixed partial salt containing calcium cations and alkali or quaternary ammonium cations of a lower alkyl vinyl ether-maleic anhydride type copolymer. The mixed salt copolymer is stated to be a water-insoluble but water-sensitized copolymer.

U.S. Pat. No. 3,736,274 teaches a dental fixative composition which contains a lower alkyl vinyl ether-maleic anhydride polymeric material, a polymeric N-vinyl lactam and a sodium carboxymethyl cellulose. The carboxymethyl cellulose prevents the maleic anhydride copolymer—N-vinyl lactam complex from completely precipitating when placed in water.

U.S. Pat. No. 3,868,432 teaches an anhydrous denture adhesive composition which is a mixture of a cationic polymeric component which is a copolymer of an acrylamide and an anionic synthetic gum component which can be a copolymer of maleic acid with vinyl lower alkyl ether.

The use of polyethylene oxide as a denture adhesive is described in U.S. Pat. No. 2,978,812.

It is the object of this invention to provide new and improved denture fixative compositions which exhibit sufficient cohesive strength to resist stresses such as those that occur upon mastication, which retain their fixative properties for prolonged periods of time and which exhibit resistance to the extreme environmental temperature changes encountered in use.

This and other objects of the invention will become apparent to those skilled in the art from the following detailed description.

SUMMARY OF THE INVENTION

This invention relates to denture fixative compositions and more particularly to such compositions which contain hydroxypropyl cellulose and a partially neutralized, optionally crosslinked, polyacrylic acid or a precursor combination thereof, or partially neutralized copolymers of maleic acid or anhydride and alkyl vinyl ethers which are optionally partially crosslinked, or a precursor combination thereof, and/or polyethylene oxide.

DETAILED DESCRIPTION OF THE INVENTION

The denture fixative compositions of the present invention can be formulated in powder, liquid, film and cream forms which, when in contact with saliva, develop a high degree of tack and uniform viscous mucilages of high cohesive strength and which, when spread over the denture-mucosa interface, provide superior denture stabilizing properties. The compositions contain a denture fixative together with an excipient therefor. Typical materials within the scope of such excipients include flavoring agents, coloring agents, preservatives and thickeners. Also other water soluble polymers such as xanthan gum, carboxymethylcellulose, methylcellulose and hydroxypropyl guar, and vehicles such as petrolatum, mineral oil and the like in cream-type formulations, and non-toxic anti-caking agents such as silica, magnesium stearate, talc, dicalcium phosphate anhydrous and the like can be present. The compositions can also contain, if desired, other known denture fixatives.

The denture fixative is a combination of hydroxy-propyl cellulose with a partially neutralized, optionally crosslinked polyacrylic acid or precursor combination thereof or certain partially neutralized, optionally crosslinked lower alkyl vinyl ether-maleic acid or anhydride copolymers, or precursor combination thereof, and/or polyethylene oxide. The hydroxypropyl cellulose employed is a non-ionic, water-soluble cellulose ether having an average molecular weight of about 50,000 to about 1,500,000 and preferably about 500,000 to about 1,000,000. This cellulose ether is commercially available and is manufactured by reacting alkali cellulose with propylene oxide at elevated temperatures and pressures which, in effect, substitutes propylene oxide by etherification at the three reactive hydroxyls present on each anhydroglucose unit of the cellulose chain in such a way that the hydroxypropyl substituent groups are almost entirely composed of secondary hydroxyl groups. The secondary hydroxyl groups are available for further reaction with propylene oxide and this results in the formation of side chains containing more than one mol of combined propylene oxide. The preferred hydroxypropyl cellulose used in the practice of the present invention preferably has a degree of substitution of propylene oxide groups in the range of about 2–4 for each anhydroglucose unit.

The hydroxypropyl cellulose described above will reversibly precipitate in aqueous media at temperatures in the range of about 30°–60° C. depending upon the presence of other materials in the solution. The form in which the cellulose precipitates depends on such other materials and also upon the molecular weight of the polymer. The precipitation temperature is lower in the presence of relatively high concentrations of other dissolved materials that compete for water in the system and is higher in the presence of organic compounds which are a solvent for the hydroxypropyl cellulose thermoplastic polymer.

The mucilages formed by the hydrated hydroxypropyl cellulose polymer in the present invention have the added advantage of imparting to the formulation a measure of hot liquid resistance because the thermoplastic polymer will precipitate to form a stringy viscous mucilage rather than be washed away when subjected to extreme environmental temperature changes such as those that occur in the oral cavity during such common actions as drinking coffee, tea or other hot beverages. Because the precipitation temperature of the polymer in the present compositions fall in a range very close to body temperature and because a denture fixative to remain effective must not be washed from its position by the dynamic fluid environment of the mouth, the denture fixative compositions incorporating the hydroxypropyl cellulose offer improved stabilization and retention properties for prolonged periods of time.

The derivatives of polyacrylic acid used in the present invention are those which, in the form of a 1% aqueous solution, exhibit a pH of at least 4.5 and preferably about 5.0 to 7.0. These polyacrylic acid derivatives are prepared by the neutralization and optional crosslinking of at least 10% and up to about 90% of the total number of initial carboxyl groups in the polyacrylic acid.

The polyacrylic acid used in the present invention is also known as carboxypolymethylene or carboxyvinyl polymer and has a repeating unit of the formula

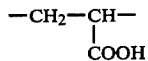

Such polyacrylic acids have molecular weights of about 500,000 to about 5,000,000, preferably about 2,000,000 to 4,000,000 and most preferably about 3,000,000.

The crosslinking agents employed are the dentally (orally) acceptable salts, oxides and bases of divalent cations and/or polyhydroxy compounds. The preferred divalent cations are alkali earth metal cations and most preferably magnesium and calcium, although other divalent cations can also be employed. Typical polyhydroxy compounds include glycerin, propylene glycol, ethylene glycol, tetramethylene glycol and the like and generally have 2 to about 6 carbon atoms and preferably 2–3 hydroxyl groups. The preferred polyhydroxy compounds are glycerin and propylene glycol.

The neutralizing agents which can be employed in the present invention are the dentally acceptable salts, oxides and bases of monovalent cations. Such cations are preferably alkali metal cations and most preferably sodium and potassium cations, although other monovalent cations can also be used. The anions of the salt and bases can be such diverse materials as hydroxide, acetate, lactate, gluconate, carbonate, and the like. It will be appreciated that any neutralization or crosslinking agent which is used must be dentally acceptable and any material which forms toxic or irritating by-products should be avoided.

The neutralizing agents and crosslinking agents are employed in an amount sufficient to either neutralize or crosslink about 20–90% of the total number of initial carboxy groups in the polyacrylic acid. The crosslinking agents are incorporated in sufficient quantity to crosslink about 0–80% of the total initial carboxy groups and the neutralizing agent in an amount sufficient to neutralize about 10–70% of the initial carboxyl groups. The crosslinking agents are preferably used in an amount sufficient to crosslink about 15–65% of the total initial carboxy groups and the neutralizing agent in an amount sufficient to neutralize about 10–50% when the crosslinking agent is a divalent salt and about 20–60% when the crosslinking agent is a polyhydroxyl compound.

The relative proportions of divalent to monovalent cations, as well as the quantity of polyhydroxy compound to be incorporated with the polyacrylic acid are major factors affecting the characteristics of the resulting reaction product such as its degree of water sensitivity and solubility, its water absorption capacity and its rates of hydration and dissolution, as well as other properties such as the cohesive and adhesive strength of the gels formed during hydration of the derivative. Relatively small changes in proportions can have a significant effect on the performance profile of the polyacrylic acid derivative as a denture fixative. Moreover, the characteristics of the derivative which are the result of the neutralization reaction with the monovalent cation can further be modified by the appropriate selection of the particular salt, oxide or base chosen to serve as a neutralizing agent. Appropriate optimization to achieve a desired balance of properties in accordance with the parameters described above is well within the skill of those working within this art. However, it is presently preferred that the divalent to monovalent cation mole ratio be in the range of about 1:4 to 4:1, most preferably about 1:2.5 to 2.5:1, and that the polyhydroxy compound be employed in quantities sufficient to react with up to about 30% of the total initial carboxyl groups in the polymer and most preferably less than about 20%. Of course, various mixtures of neutralizing agents and crosslinking agents can be employed.

The polyacrylic acid derivatives can also be utilized in the form of a precursor composition therefor. A particularly convenient embodiment contains the partially neutralized salt of polyacrylic acid together with the intended crosslinking agent and the desired crosslinking reaction is permitted to occur in situ when the fixative composition is exposed to saliva. Alternatively, the composition can contain the partially crosslinked polyacrylic acid with the intended neutralizing agent but in this instance, more neutralizing agent should be employed than in the embodiment just mentioned. In another alternative, appropriate neutralizing and optional crosslinking agents can be incorporated with the polyacrylic acid in anhydrous formulations. In the latter instance, the corresponding reactions will occur spontaneously in the presence of water, making the system particularly suitable for use in denture adhesive or fixative compositions. It will be appreciated that such compositions are generally formulated incorporating an anhydrous vehicle such as petrolatum or mineral oil in cream formulations in order to protect their water-activated ingredients from premature contact with moisture. In such formulations, additionally, it is judicious to avoid the use of neutralizing and crosslinking agents which generate a pH higher than about 10 immediately after the formulation is in contact with saliva and thereby increase the risk of irritation and/or injury to the oral mucosa.

The extremely hydrophilic nature of the described polyacrylic acid derivatives and their ability to rapidly generate viscosity upon contact with water, render them ideal materials to use in combination with the hydroxypropyl cellulose of the present invention. Formulations containing both will rapidly generate tacky, viscous, uniform mucilages of high cohesive strength which are capable of acting in prolonged stabilization and retention of the denture in vivo.

The partially neutralized copolymer of a lower alkyl-vinyl ether and maleic acid or anhydride is that which, in the form of a 1% aqueous solution, has a pH of at least about 4.5 and preferably at least about 5. The copolymer can also be partly crosslinked.

The copolymers of the lower alkyl vinyl ether and maleic acid or anhydride used in the present invention have specific viscosities in the range of about 1.5 to about 3.5. Such copolymers have the repeating structural unit

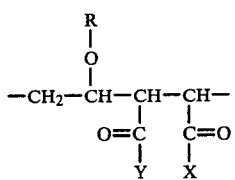

wherein X and Y separately each represent a hydroxyl moiety or together represent a single oxygen. R represents a lower alkyl moiety of 1 to about 5 carbon atoms. The copolymers are obtained by copolymerizing a lower alkyl vinyl ether monomer with maleic acid or anhydride. Suitable copolymers are commercially available.

Typical lower alkyl vinyl ethers include methyl vinyl ether, ethyl vinyl ether, divinyl ether, propyl vinyl ether, isobutyl vinyl ether and the like. It will be appreciated that the copolymers can also contain mixtures of the vinyl ethers.

The copolymers employed in the present invention are neutralized and optionally crosslinked such that up to about 90% of the total number of initial carboxyl groups in the copolymer are consumed. In determining the total number of initial carboxyl groups, the anhydride radical is considered as having two such groups. Thus, the copolymers as used in the present invention will contain at least about 10% of unreacted initial carboxyl groups.

The neutralization agents and crosslinking agents employed in conjunction with the copolymer are the same agents employed in conjunction with the polyacrylic acid described above. The neutralization agents are employed in a quantity sufficient to react with about 10-70% of the total number of initial carboxyl groups in the copolymer and preferably about 20-60%. When employed, the crosslinking agents are used in quantities sufficient to crosslink up to 50% of the total number of initial carboxyl groups and preferably in amounts sufficient to crosslink about 5-35% of the initial carboxyl groups. If desired, a partially neutralized copolymer can be combined with the intended crosslinking agent in the denture fixative composition and the crosslinking reaction permitted to occur in situ when the denture fixative formulation is exposed to saliva.

The polyethylene oxide used in this invention is a well-known denture fixative and is commercially available having a molecular weight of 500,000 to 5,000,000 and preferably about 1,000,000 to 3,000,000. It can be employed in place of, in whole or in part, the polyacrylic acid or the copolymer. When it replaces a part of the acid or copolymer, the polyethylene oxide will usually be about 5-25% of the active fixative and preferably about 8-20%.

The denture fixative combination of the hydroxypropyl cellulose and the polyacrylic acid derivatives or copolymer or polyethylene oxide are incorporated into the denture fixative composition in an effective fixative amount. The amount will vary considerably, depending on the particular hydroxypropyl cellulose, the particular polyacrylic acid derivative, the particular vinyl ether-maleic acid or anhydride copolymer, the degree of neutralization, the degree of crosslinking, the presence and the amount of the polyethylene oxide and the other constituents of the fixative composition. In general, the fixative is about 10-70 weight percent or more of the denture fixative composition and preferably about 15-50 weight percent. When the denture fixative composition is formulated in the form of a film, the fixative can be up to about 99 weight percent of the film. In general, the hydroxypropyl cellulose will constitute about 10-80% of the fixative mixture and preferably about 30-70% weight percent.

In order to further illustrate the present invention, various illustrative examples are set forth below. In these examples, as well as throughout the specification and claims, all parts and percentages are by weight and all temperatures in degrees Celsius unless otherwise specified.

EXAMPLES 1-2

A mixture of 15 parts of calcium hydroxide and 150 parts of a commercially available copolymer of methyl-vinyl ether-maleic anhydride (PVM/MA) having a specific viscosity of 3.2 was dissolved in 620 parts of water in a reaction kettle. Thereafter, 25 parts of sodium hydroxide in 100 parts of water were added slowly to the rapidly agitated solution. The resulting mixture was heated to 45° C. and held at this temperature for one hour. The resulting product was then dried and ground through a 100 mesh sieve (U.S. Standard Sieve Series) to yield a powder which had a packed bulk density of 0.7 g/ml and which had a pH of 5.5 in the form of a 1% aqueous solution.

A cream denture fixative composition was prepared by mixing the following ingredients together:

| | |
|---|---|
| Na/Ca PVM/MA | 20 parts |
| Hydroxypropyl cellulose | 20 parts |
| Mineral oil and petrolatum | 59 parts |
| Flavor, color and preservative | 1 part |

A powder denture fixative was prepared by blending together the following ingredients:

| Na/Ca PVM/MA | 35 parts |
|---|---|
| Hydroxypropyl cellulose | 30 parts |
| Dicalcium phosphate (filler) | 34 parts |
| Flavor, color, preservative | 1 part |

EXAMPLES 3-4

There was introduced into and dissolved in a reaction kettle containing 740 parts of water, 10 parts of glycerin and 150 parts of a copolymer of ethyl vinyl ethermaleic anhydride (PVE/MA) which had a specific viscosity of 2.6. 30 parts of sodium hydroxide in 150 parts of water were slowly added to the rapidly agitated solution and the resulting mixture heated to 45° C. where it was maintained for one hour. The resulting product was then dried, ground and screened through a 100 mesh sieve to obtain a powder having a packed density of 0.75 g/ml and a pH of 6 as a 1% aqueous solution.

A cream denture fixative composition was prepared with the foregoing partially neutralized and crosslinked copolymer by mixing together the following ingredients:

| Na/glycerin PVE/MA | 25 parts |
|---|---|
| Hydroxypropyl cellulose | 15 parts |
| Mineral oil and petrolatum | 59 parts |
| Flavor, color and preservative | 1 part |

A liquid denture fixative composition was prepared by mixing together the following components:

| Na/glycerin PVE/MA | 18 parts |
|---|---|
| Hydroxypropyl cellulose | 16 parts |
| Mineral oil/polyethylene base | 65 parts |
| Flavor, color, preservative | 1 part |

EXAMPLE 5

A copolymer of ethyl vinyl ether-maleic anhydride (PVE/MA) having a specific viscosity of 3.2 in an amount of 200 parts was dissolved in 600 parts of water in a reaction kettle. The solution was rapidly agitated and 60 parts of potassium hydroxide in 140 parts of water were added slowly to the rapidly agitated solution. The mixture was then heated to 45° C., held at this temperature for one hour and the resulting product, dried, ground and screened through a 100 mesh sieve. The resulting powder had a packed density of 0.74 g/ml and a 1% aqueous solution had a pH of 6.3. The resulting partially neutralized copolymer was incorporated into a cream denture fixative composition by mixing 27 parts of the K PVE/MA, 13 parts of hydroxypropyl cellulose, 59 parts of mineral oil and petrolatum, and 1 part of flavor, color and preservative.

EXAMPLE 6

A film denture fixative was prepared by mixing 40 parts of the partially neutralized copolymer described in Example 5 with 59 parts of hydroxypropyl cellulose and 1 part of color, flavor, antioxidant and preservative additives. 120 parts of the resulting mixture were dissolved in a mixture containing 472 parts of water and 8 parts of glycerin. A viscous solution resulted which was heated to 45° C. and deaerated under vacuum before casting and drying at a temperature of 55°±5° C. The resulting film showed excellent flexibility and had a thickness of 0.006 inch (6 mils).

EXAMPLE 7

A polyacrylic acid having an average molecular weight of 3,000,000 was slowly added with vigorous agitation to a slurry of sodium hydroxide and calcium hydroxide in an aqueous methanol solution. After filtration and drying, the resulting product was ground and screened through a 100 mesh sieve. The pH of a 1% aqueous solution of the partially neutralized and crosslinked polyacrylic acid was 5.6.

A liquid denture adhesive was prepared by compounding 10 parts of the Na/Ca polyacrylic acid, 30 parts of hydroxypropylcellulose ($10^6$ MW), 58.5 parts of mineral oil and 1.5 parts of flavor, color and preservative.

EXAMPLE 8

A cream denture fixative composition was prepared by first blending 25 parts of hydroxypropylcellulose (750,000 MW) with 15 parts of Na polyacrylic acid (pH 6.6). The powder mix was then mixed with flavor, color and preservative additives and a petrolatum base to form a smooth, homogeneous cream.

EXAMPLE 9

Ten parts of a partially neutralized and crosslinked sodium/glycerin salt of polyacrylic acid (pH 6.6) was mixed with 30 parts of hydroxypropylcellulose ($10^6$ MW), 15 parts of sodium carboxymethylcellulose, 54 parts of mineral oil and petrolatum and flavor, color and preservative additives q.s. to form a paste denture fixative composition.

EXAMPLE 10

A liquid denture adhesive formulation was prepared by combining 10 parts of hydroxypropylcellulose ($10^6$ MW), 25 parts of the partially neutralized and crosslinked sodium/glycerin salt of polyacrylic acid (pH 6.4), 64.3 parts of mineral oil and 0.7 part of flavor, color and preservative additives.

EXAMPLE 11

A cream denture adhesive formulation was prepared by compounding the partially neutralized and crosslinked potassium magnesium salt of polyacrylic acid (pH 5.8) in an amount of 32 parts with 10 parts of hydroxypropylcellulose (300,000 MW) 56 parts of petrolatum and color, flavor and preservative additives q.s.

EXAMPLE 12

A blend of 40 parts hydroxypropylcellulose ($10^6$ MW), 59 parts of sodium polyacrylic acid (pH 6.3) and 1 part of color, flavor, antioxidant and preservative additives was prepared. 120 parts of the powder blend was dissolved in 472 parts of water and 8 parts of glycerin. The viscous solution was heated to 45° C., deaerated under vacuum, cast and then dried at a temperature of 55°±5° C. The resulting film had a thickness of 0.006 inch (6 mils) and demonstrated good flexibility.

EXAMPLE 13

A denture adhesive cream was compounded from 28 parts hydroxypropylcellulose ($10^6$ MW), 12 parts sodium/glycerin polyacrylic acid (pH 5.4), 2 parts flavor, color and preservative and 58 parts of petrolatum and mineral oil. The formulation was found to demonstrate good denture stabilizing properties.

EXAMPLES 14-15

Two denture fixative powder formulations were manufactured by mixing the following blends with 30 parts of dicalcium phosphate anhydrous, 2 parts flavor and preservative and 0.5 part silicon dioxide:

| | |
|---|---|
| EXAMPLE 14: | |
| Hydroxypropylcellulose ($10^6$ MW) | 30 Parts |
| Potassium polyacrylic acid (pH 6.6) | 37.5 Parts |
| EXAMPLE 15: | |
| Hydroxypropylcellulose ($10^6$ MW) | 20 Parts |
| Sodium magnesium polyacrylic acid (pH 5.8) | 47.5 Parts |

EXAMPLE 16

A liquid denture fixative composition was prepared by blending the following mixture with 65 parts of a mineral oil base:

| | |
|---|---|
| Sodium glycerin polyacrylic acid (pH 5.4) | 15 Parts |
| Hydroxypropylcellulose ($10^6$ MW) | 18.5 Parts |
| Flavor, color and preservative | 1.5 Parts |

EXAMPLES 17-18

Two denture fixative powder formulations were manufactured by mixing the following blends with 36 parts of dicalcium phosphate anhydrous and 1 part of flavor and preservative.

| | |
|---|---|
| EXAMPLE 17: | |
| Hydroxypropylcellulose ($10^6$ MW) | 42 Parts |
| Polyethylene oxide ($2 \times 10^6$ MW) | 21 Parts |
| EXAMPLE 18: | |
| Hydroxypropylcellulose ($10^6$ MW) | 39 Parts |
| Polyethylene oxide ($2 \times 10^6$ MW) | 13 Parts |
| Potassium polyacrylic acid (pH 6.6) | 11 Parts |

Various changes and modifications can be made in the products of this invention without departing from the spirit and the scope thereof. Various embodiments which have been set forth herein were for the purpose of further illustrating the invention but were not intended to limit it.

What is claimed is:

1. A denture fixative composition comprising a dentally acceptable excipient and an effective fixative amount of a fixative mixture comprising hydroxypropylcellulose and (a) polyacrylic acid partially neutralized by at least one dentally acceptable monovalent cation such that about 20-90% of the initial carboxy groups have been neutralized and 0-80% of the initial carboxy groups have been crosslinked by at least one dentally acceptable agent selected from the group consisting of divalent cations and polyhydroxy compounds, wherein a 1% aqueous solution of said polyacrylic acid has a pH of at least about 4.5, or a precursor combination of polyacrylic acid, neutralizing agent and crosslinking agent adapted to form said polyacrylic acid in an aqueous environment; (b) partially neutralized lower alkyl vinyl ether-maleic acid or anhydride copolymer, which has been partially neutralized by at least one dentally acceptable monovalent cation and 0-50% of the initial carboxy groups have been crosslinked by at least one dentally acceptable agent selected from the group consisting of divalent cations and polyhydroxy compounds such that up to about 90% of the total number of initial carboxyl groups have been neutralized or crosslinked, wherein a 1% aqueous solution of said neutralized copolymer has a pH of at least about 4.5, or a precursor combination of said copolymer, neutralizing agent and crosslinking agent adapted to form said partially neutralized copolymer in aqueous environment; (c) polyethylene oxide; or (d) a combination of (c) with (a) or (b).

2. The denture fixative composition of claim 1, wherein said member of said group is said copolymer and has a specific viscosity of about 1.3-3.5 prior to neutralization, contains at least about 10% unreacted initial carboxyl groups and said solution therefor has a pH of at least about 5.

3. The denture fixative composition of claim 2, wherein about 10-70% of the initial carboxyl groups of said copolymer have been neutralized by a monovalent cation.

4. The denture fixative composition of claim 3, wherein said monovalent cation is sodium or potassium and said lower alkyl moiety is methyl or ethyl.

5. The denture fixative composition of claim 4, wherein said copolymer is partly crosslinked and said divalent cation is calcium or magnesium and said polyhydroxy compound contains 2 to about 6 carbon atoms.

6. The denture fixative composition of claim 5, wherein said member of said group is said partially neutralized copolymer containing a crosslinking agent.

7. The denture fixative composition of claim 1, wherein said member of said group is said copolymer precursor combination and comprises copolymer, neutralizing agent and crosslinking agent.

8. The denture fixative composition of claim 1, wherein said member of said group is said polyacrylic acid having an average molecular weight of about 500,000 to 5,000,000, said divalent cation is an alkaline earth metal cation, said polyhydroxy compound has 2 to about 6 carbon atoms and said monovalent cation is an alkali metal cation.

9. The denture fixative composition of claim 8, wherein said polyacrylic acid has an average molecular weight of about 2,000,000-4,000,000, said monovalent cation is sodium or potassium, said divalent cation is magnesium or calcium and said polyhydroxy compound is glycerin or propylene glycol.

10. The denture fixative composition of claim 9, wherein the amount of neutralizer is sufficient to neutralize about 10-70% of the initial carboxyl groups.

11. The denture fixative composition of claim 10, wherein the amount of neutralizer is sufficient to neutralize about 20-60% and the amount of crosslinker is sufficient to crosslink about 5-35% of the initial carboxy groups.

12. The denture fixative composition of claim 1, wherein said member of said group is said polyacrylic acid precursor combination and comprises a partially neutralized polyacrylic acid and a crosslinking agent.

13. The denture fixative composition of claim 1, wherein said member of said group is said polyacrylic acid precursor combination and said precursor combination comprises polyacrylic acid, a neutralizing agent and a crosslinking agent.

14. The denture fixative composition of claim 1, wherein said member of said group is said polyethylene oxide.

15. The denture fixative composition of claim 1, wherein said member of said group is said combination of polyethylene oxide and said polyacrylic acid or precursor thereof.

16. The denture fixative composition of claim 1, wherein said member of said group is said combination of polyethylene oxide and said copolymer.

* * * * *